United States Patent [19]

Kanai

[11] Patent Number: 5,230,692
[45] Date of Patent: Jul. 27, 1993

[54] INTRA-AORTIC BALLOON PUMP

[75] Inventor: Naritoshi Kanai, Anjo, Japan

[73] Assignees: Aisin Seiki Kabushiki Kaisha, Aichi; Kabushiki Kaisha Shisangyo-Kaihatsu, Tokyo, both of Japan

[21] Appl. No.: 764,848

[22] Filed: Sep. 24, 1991

[30] Foreign Application Priority Data

Sep. 30, 1990 [JP] Japan .................... 2-102569[U]

[51] Int. Cl.⁵ .............................................. A61B 17/12
[52] U.S. Cl. ............................................ 600/18; 600/16
[58] Field of Search ................................... 600/16, 18

[56] References Cited

U.S. PATENT DOCUMENTS

| 4,531,512 | 7/1985 | Wolvek et al. | 600/18 |
| 4,733,652 | 3/1988 | Kantrowitz et al. | 600/18 |
| 4,994,018 | 2/1991 | Saper | 600/18 |

Primary Examiner—Kyle L. Howell
Assistant Examiner—Scott M. Getzow
Attorney, Agent, or Firm—Finnegan, Henderson, Farabow, Garrett & Dunner

[57] ABSTRACT

An intra-aortic balloon pump of this invention comprises a catheter (4) which introduces a pumping media, a wrapped membrane (5) which is mounted on one end of the catheter (4), a protection sleeve (1) which accommodates the membrane (5), a sealing cap (3) which is mounted on the catheter (4) and is movable along the catheter (4), and, an intermediate member (2) which is located between the membrane (5) and the sealing cap (3) and is movable along the catheter (4) together with the membrane (5) so as to prevent the membrane (5) from unwrapping. After the intermediate member (2) is moved to the membrane (5) so that the intermediate member (2) overlaps the membrane (5), the intermediate member (2) prevents the membrane (5) from unwrapping. Therefore, the sleeve (1) can be removed from the membrane (5) without unwrapping the membrane (5). After the membrane (5) is inserted in a femoral artery through a sheath (9), the membrane (5) ascends in the descending abdominal aorta toward the failing heart. During the percutaneous balloon insertion, the intermediate member (2) prevents the membrane (5) from unwrapping. Therefore, the membrane (5) does not become wrinkled at an outside end (13) of the sheath (9). Thus, the balloon pump is inserted in the sheath (9) easily and smoothly.

8 Claims, 6 Drawing Sheets

INFLATION

DEFLATION

INTRA-AORTIC BALLOON PUMP

BACKGROUND OF THE INVENTION

This invention relates to an intra-aortic balloon pump which is inserted in an aorta percutaneously so as to assist the blood flow through a failing heart and to the body.

A percutaneous balloon pump includes a membrane and a catheter. The membrane is mounted on a proximal end of the catheter. The balloon pump is furled by wrapping the membrane around the catheter before insertion. Then, the balloon pump is inserted through a sheath into a femoral artery along a guide wire which is inserted in advance. The membrane ascends in a descending abdominal aorta toward the failing heart. After the membrane is properly positioned in the aorta, a sealing rubber cap which tightly surrounds the catheter is pressed to the sheath. The sealing rubber cap connects the catheter to the sheath in fluid tight manner. The sealing rubber cap closes an opening between the catheter and the sheath so as to prevent the blood from bleeding through the sheath. When pumping starts, the membrane immediately unwraps due to introduction of the pumping media and functions as an intra-aortic balloon. As shown in FIGS. 7 and 8, during the pumping, the membrane is inflated and deflated alternately so as to assist the blood flow through the failing heart and to the body.

While the wrapped membrane is inserted into the sheath, the membrane tends to be unwrapped and also tends to be deformed. FIG. 6 shows the membrane (5) which is inserted into a sheath (9). As described above, the membrane (5) has to be unwrapped when pumping starts. Therefore, the membrane (5) can be unwrapped and deformed very easily. Thus, even if the membrane (5) is inserted very carefully into the sheath (9), the membrane (5) often becomes wrinkled at an outside end (13) of the sheath (9). When the membrane (5) is inserted into the femoral artery, these wrinkles are gradually moved toward the catheter (4) and become larger and larger. In the worst situation, due to the large wrinkles, the balloon pump is difficult to insert into the sheath (9).

SUMMARY OF THE INVENTION

Accordingly, one of the objects of this invention is to obviate the above conventional drawbacks.

Further, one of the objects of this invention is to make percutaneous balloon insertion easier.

Furthermore, one of the objects of this invention is to prevent blood from bleeding through a sheath after percutaneous balloon insertion.

To achieve the above objects, an intra-aortic balloon pump of this invention comprises a catheter (4) which introduces the pumping media, a wrapped membrane (5) which is mounted on one end of the catheter (4), a protection sleeve (1) which accommodates the membrane (5), a sealing cap (3) which is mounted on the catheter (4) and is movable along the catheter (4), and, an intermediate member (2) which is located between the membrane (5) and the sealing cap (3) and is movable along the catheter (4) together with the membrane (5) so as to prevent the membrane (5) from unwrapping.

Before using the balloon pump, the membrane (5) is covered by the protection sleeve (1). After the intermediate member (2) is moved to the membrane (5) so that the intermediate member (2) is overlaps the membrane (5), the intermediate member (2) prevents the membrane (5) from unwrapping. Therefore, the sleeve (1) can be removed from the membrane (5) without unwrapping the membrane (5). After the membrane (5) is inserted in a femoral artery through a sheath (9), the membrane (5) ascends in the descending abdominal aorta toward the failing heart. While the membrane (5) is inserted into the sheath (9), the intermediate member (2) reaches an outside end (13) of the sheath (9). During the percutaneous insertion of the balloon pump, the intermediate member (2) prevents the membrane (5) from unwrapping. Therefore, the membrane (5) does not become wrinkled at an outside end (13) of the sheath (9). Thus the balloon pump is inserted in the sheath (9) easily and smoothly.

BRIEF DESCRIPTION OF THE DRAWINGS

Those and other objects and features of this invention will be apparent from the description which follows hereinafter with reference to a preferred embodiment shown in the accompanying drawings in which.

DETAILED DESCRIPTION OF THE PREFERRED EMBODIMENT

Figure 1:
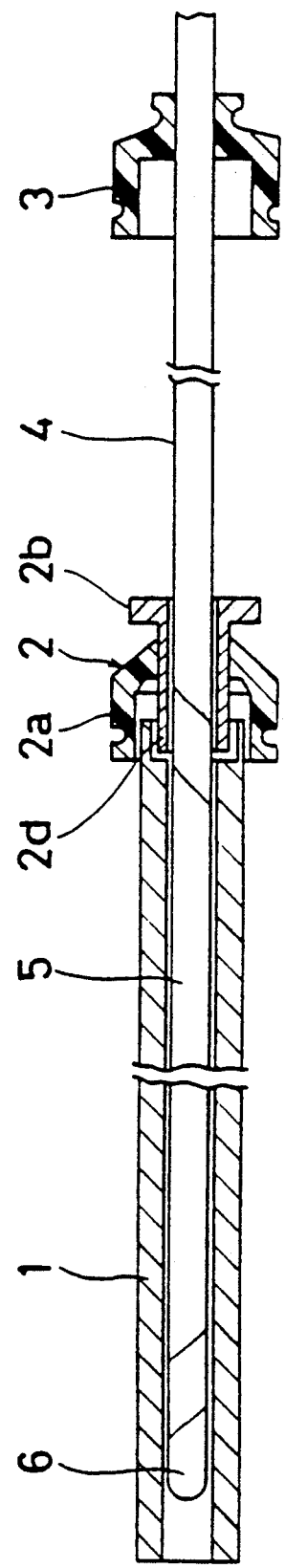
FIG. 1 is a cross sectional view showing a preferred embodiment of this invention.

FIG. 1 shows a preferred embodiment of the present inventions before it is used. In the accompanying drawings, dimensions are enlarged compared their actual dimensions so as to show detail.

A distal end of a membrane (5) is mounted to one end of a catheter (4). The membrane (5) is furled by wrapping it around the catheter (4) and is covered by a protection sleeve (1). The catheter (4) passes through a sealing rubber cap (3).

Figure 2:
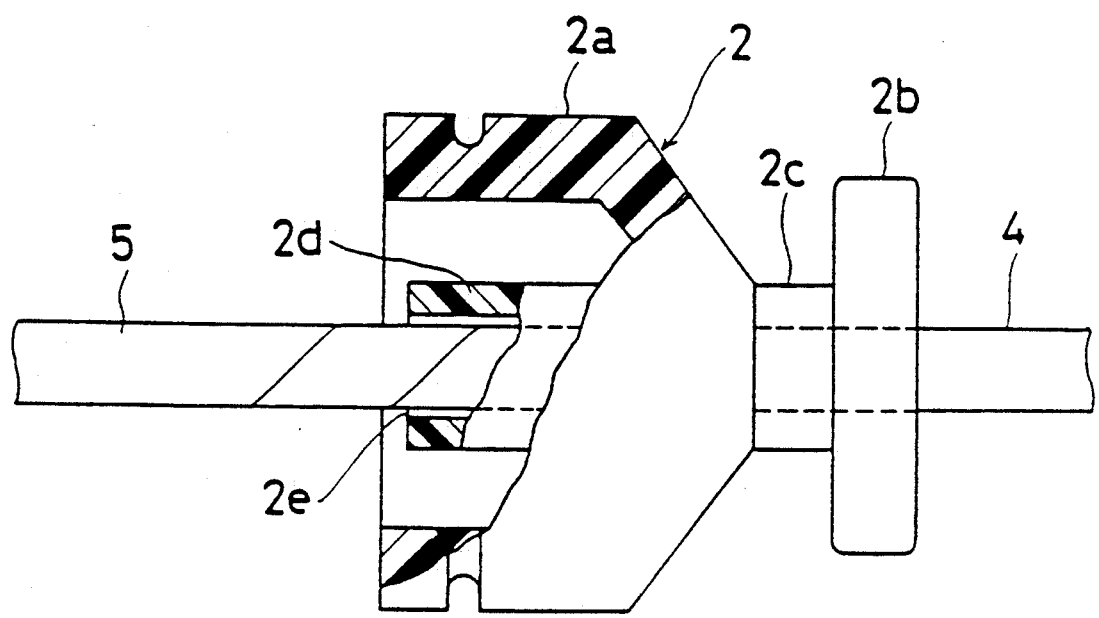
FIG. 2 is a detailed side view of the intermediate member shown in FIG. 1.
Figure 6:
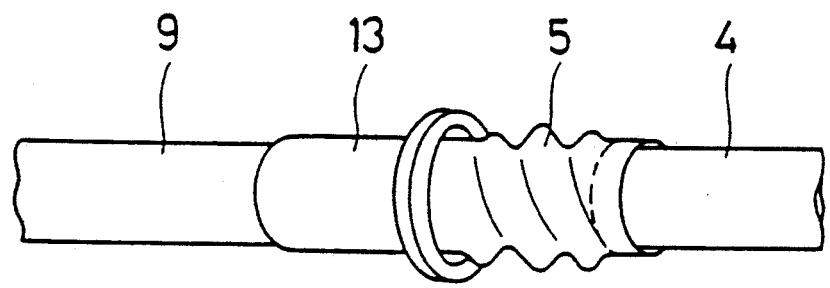
FIG. 6 is a perspective view illustrating one of the drawbacks of the conventional apparatus.

An intermediate member (2) is located at a connecting portion between the distal end of a membrane (5) and the catheter (4). The intermediate member (2) projects toward the membrane (5) from the connecting portion. FIG. 2 shows details of intermediate member (2). The intermediate member (2) includes a tube (2c) which is made from a hard synthetic resin and a side column (2a) which is made from soft synthetic resin. The side column (2a) is provided integrally to the tube (2c). The intermediate member (2) has a central bore (2e) through which the wrapped membrane (5) can be passed easily. The central bore (2e) prevents the wrapped membrane (5) from unwrapping. A flange portion (2b) is provided on the tube (2c). The flange portion (2b) is utilized for connecting the intermediate member (2) to the sealing rubber cap (3). The column (2a) receives an outside end (13) of the sheath (9) (See FIG. 4). The column (2a) projects toward the sheath (9) so as to connect the intermediate member (2) tightly to the outside end (13) of the sheath (9).

The intermediate member (2) can be moved along the catheter (4) easily compared with the sealing cap (3). However, as shown in FIGS. 1 and 2, when the intermediate member (2) overlaps on the wrapped membrane (5), the intermediate member (2) can not be moved along the catheter (4) easily since the intermediate member (2) contacts with the wrapped membrane (5).

The sealing rubber cap (3) has a cup-shape. The sealing rubber cap (3) opens toward the intermediate member (2). The catheter (4) passes through the sealing rubber cap (3). The sealing rubber cap (3) can be moved along the catheter (4). However, the sealing rubber cap (3) surrounds the catheter (4) in a fluid tight manner due to elasticity of sealing rubber cap (3).

Figure 3:
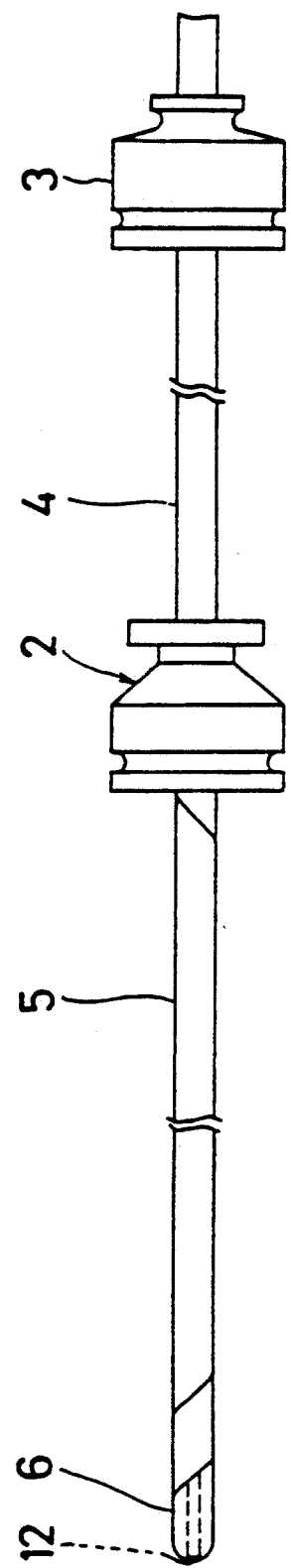
FIG. 3 is a side view of a preferred embodiment of the present invention before insertion into a patient.
Figure 4:
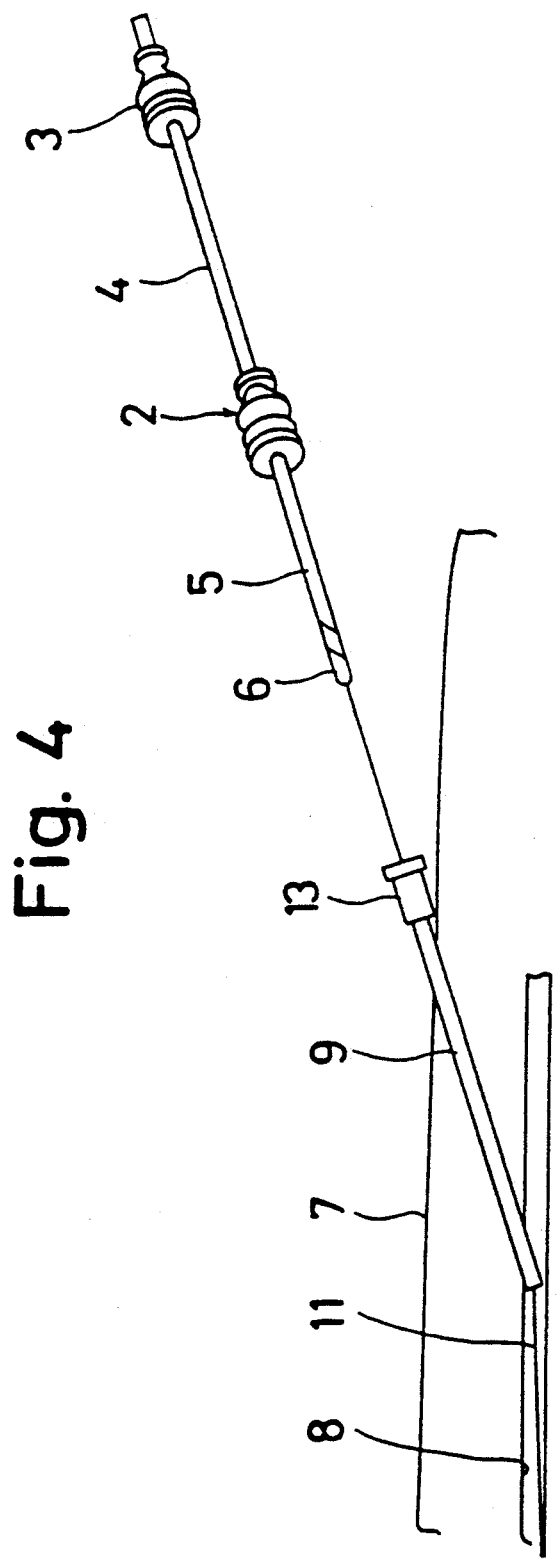
FIG. 4 is a perspective view showing percutaneous insertion of a preferred embodiment of the present invention into a patient.

Before the membrane (4) is inserted into a femoral artery (8), the protection sleeve (1) is removed from the membrane (4). FIG. 3 shows the membrane (4) after removing the protection sleeve (1). As shown in FIG. 4, a sheath (9) is inserted from outside of the human body (7) to the femoral artery (8) which is connected to the descending abdominal aorta. A guide wire (11) is drawn out from a proximal end (12) of the catheter (4). The guide wire (11) is inserted from a Y-shaped connector (10) into the catheter (4) (See FIG. 5). Then the guide wire (11) passes through the catheter (4). The guide wire (11) ascends from the femoral artery (8) to a descending abdominal aorta. After drawing out the guide wire (11), upon insertion of the membrane (5), the membrane (5) is guided by the guide wire (11) and the sheath (9).

During the insertion of the membrane (5), the intermediate member (2) reaches to the outside end (13) of the sheath (9). Then the outside end (13) of the sheath (9) is surrounded by the column (2a) so that the intermediate member (2) is connected to the outside end (13) of the sheath (9). Thus, the intermediate member (2) is tightly connected to the sheath (9).

Next, the membrane (5) is guided toward a failing heart with the catheter (4) and guide wire (11) so that the membrane (5) obtains a proper position. During the insertion of the balloon pump, the membrane (5) and the catheter (4) are transferred into the sheath (9) through the intermediate member (2). An extending portion (2d) of the tube (2c) prevents the membrane (5) from unwrapping and becoming wrinkled at the outside end (13) of the sheath (9). The balloon pump can be inserted very easily and smoothly into the sheath (9), since the membrane (5) is transferred to the femoral artery (8) with a guidance of the extending portion (2d) of the intermediate member (2).

Once the membrane (5) obtains the proper position, the insertion of the balloon pump is over. Then, the sealing rubber cap (3) is moved toward the intermediate member (2) so as to connect the sealing rubber cap (3) to the intermediate member (2). The connecting manner for the sealing rubber cap (3) is substantially the same as the connecting manner between the intermediate member (2) and the outside end (13) of the sheath (9).

Figure 5:
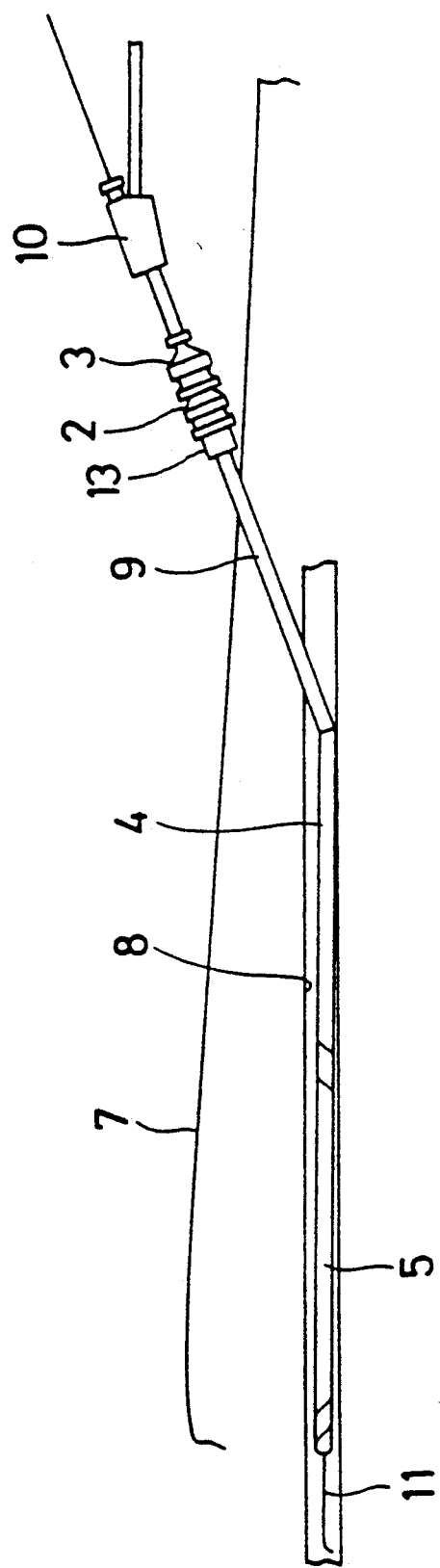
FIG. 5 is a side view of a preferred embodiment of the present invention during insertion into a patient.
Figure 7:
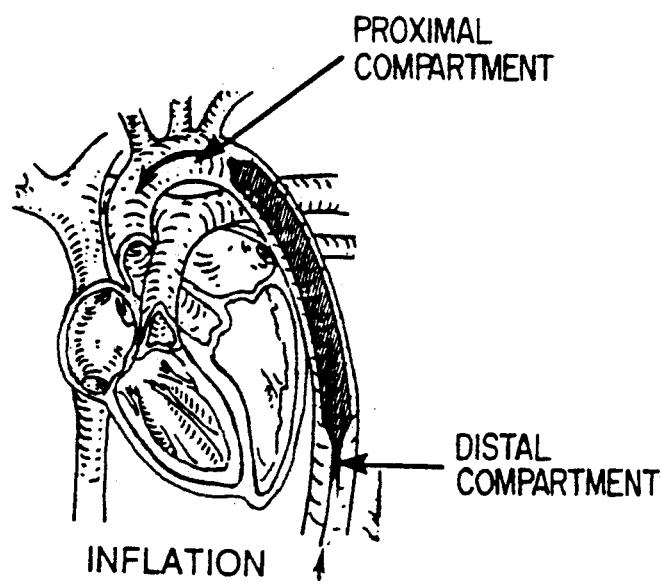
FIG. 7 is a partial cross sectional view of a failing heart which is assisted by a conventional inflated balloon pump.
Figure 8:
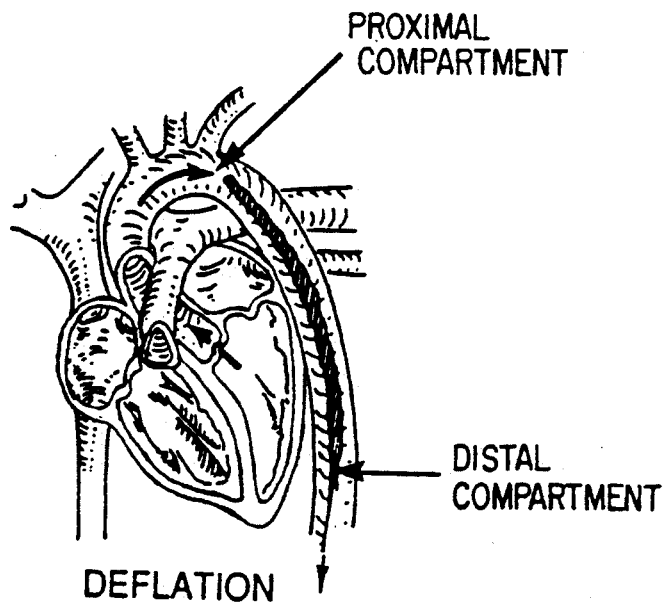
FIG. 8 is a partial cross sectional view of a failing heart which is assisted by a conventional deflated balloon pump.

As described above, the membrane (5) has been fixed at the proper position which is close to the failing heart and the preparation for pumping has been obtained. FIG. 5 shows the final position before pumping is initiated. As shown in FIG. 5, the intermediate member (2) is tightly connected to the outside end (13) of the sheath (9). Further, the sealing rubber cap (3) is tightly connected to the intermediate member (2). Furthermore, the sealing rubber cap (3) is tightly connected to the catheter (4). Thus, the sheath (9) is tightly isolated from the outside of the human body (7). Therefore, blood does not bleed through the sheath (9) after completing percutaneous balloon insertion. Before pumping is started, the guide wire (11) is removed.

Various modification may be made to the above-described embodiment without departing from the scope and spirit of this invention.

What is claimed is:

1. An intra-aortic balloon pump to be inserted in an aorta through a sheath comprising:
   a catheter for introducing a pumping media;
   a membrane wrapped on one end of the catheter;
   a protection sleeve surrounding the wrapped membrane prior to use;
   a sealing cap mounted on the catheter and movable along the catheter; and,
   an intermediate member surrounding a portion of the wrapped membrane and located between the one end of the catheter and the sealing cap, and easily movable along the catheter and the wrapped membrane so as to prevent the wrapped membrane from unwrapping.

2. The apparatus in claim (1) wherein the intermediate member further comprises:
   an extending portion having a central bore through which the wrapped membrane passes;
   a side column for connecting the intermediate member to the sheath;
   a flange portion for connecting the intermediate member to the sealing cap.

3. The apparatus in claim (2) wherein the extending portion is made from a hard synthetic resin.

4. The apparatus in claim (2) wherein the side column is made from a soft synthetic resin.

5. An intra-aortic balloon pump to be inserted in an aorta through a sheath, comprising:
   a catheter for introducing a pumping media;
   a membrane wrapped on one end of the catheter;
   a sealing cap mounted on the catheter and surrounding the catheter in a fluid tight manner;
   an intermediate member surrounding a portion of the wrapped membrane and located between the one end of the catheter and the sealing cap, for preventing the wrapped membrane from unwrapping;
   wherein the sealing cap includes means for fixing the sealing cap to the intermediate member in a fluid tight manner.

6. The apparatus in claim 5 wherein the fixing means comprises a cup-shaped rubber member.

7. An intra-aortic balloon pump to be inserted in an aorta through a sheath, comprising:
   a catheter for introducing a pumping media;
   a membrane wrapped on one end of the catheter;
   a sealing cap mounted on the catheter and surrounding the catheter in a fluid tight manner;
   an intermediate member surrounding a portion of the wrapped membrane and located between the one end of the catheter and the sealing cap, for preventing the wrapped membrane from unwrapping;
   wherein the intermediate member includes means for connecting the intermediate member to the sheath.

8. The apparatus in claim 7 wherein the connecting means comprises a side column made from a synthetic resin.

* * * * *